(12) United States Patent
O'Lenick, Jr.

(10) Patent No.: US 6,201,143 B1
(45) Date of Patent: Mar. 13, 2001

(54) FREE RADICAL POLYMERS BASED ON MEADOWFOAM ESTERS

(75) Inventor: Anthony J. O'Lenick, Jr., Dacula, GA (US)

(73) Assignee: Fan Tech Ltd., Chicago, IL (US)

(*) Notice: Subject to any disclaimer, the term of this patent is extended or adjusted under 35 U.S.C. 154(b) by 0 days.

(21) Appl. No.: 09/378,938

(22) Filed: Aug. 23, 1999

(51) Int. Cl.⁷ .................................................. C07C 233/00
(52) U.S. Cl. ................................ 554/59; 554/52; 554/224; 554/227; 554/229
(58) Field of Search ............................. 554/52, 59, 224, 554/227, 229

(56) References Cited

U.S. PATENT DOCUMENTS 5,162,472   11/1992   O'Lenick, Jr. .

*Primary Examiner*—Deborah D. Carr

(57) ABSTRACT

The present invention is directed to free radical polymers, which contain a meadowfoam ester group as one of the functional groups polymerized. The compounds of the invention are prepared by the free radical polymerization of a novel meadowfoam monomer having a reactive vinyl group and a number of other free radical polymerizable reactants. The unique structure of the meadowfoam results in polymers with oxidative stability heretofore unattainable.

20 Claims, No Drawings

FREE RADICAL POLYMERS BASED ON MEADOWFOAM ESTERS

BACKGROUND OF THE INVENTION

Field of the Invention

The present invention deals with the composition, and application of novel meadowfoam containing polymers, useful as softening, anti-tangle, and conditioning agents for use in personal care, textile and related applications. The properties of these novel compounds containing a meadowfoam ester moiety in the polymer backbone which makes them well suited for these applications is the fact that they are substantive to fibers, hair and skin and also very mild to the skin and eyes and provide protection from environmental factors like acid rain and other pollutions which come in contact with hair and skin. The incorporation of a the meadowfoam component into the molecule results in several additional desirable properties heretofore unattainable. The polymers are more elastomeric, are resistant to mal-odor formation and provide outstanding gloss and protection of the hair from environmental factors which can be damaging to the hair.

The recent availability of meadowfoam oil, with it's 20 to 22 carbon atoms and the specific location of it's double bonds, and it's reaction to make polymers results in the preparation liquid stable polymers, having outstanding emulsifying properties and are very acceptable for use in personal care applications.

Arts and Practices

The prior practices for providing softening, anti-tangle, and conditioning properties for use in personal care, textile and related applications has been incorporation of quaternary compounds. These materials have been used for many years despite some significant drawbacks including irritation, negative impact on the aquatic environment, build up and yellowing of the substrate upon which they are applied.

U.S. Pat. No. 5,162,472 to O'Lenick discloses free radical polymers which incorporate silicone into the backbone. While these materials have desirable properties, they do not form monolayers on the hair nor do they provide the protection to the hair offered by incorporating meadowfoam into the molecule.

The references cited herein are incorporated by reference to the extent applicable. Ratios and percentages are by weight and temperatures are Celsius unless otherwise stated.

THE INVENTION

Object of the Invention

It is the object of the current invention to provide a novel series of meadowfoam containing polymers. The incorporation of the critical meadowfoam group gives increased elastomeric properties, increased resistance to odor formation, lowers irritation and provides excellent antistatic, comb out properties and softening to hair and skin.

It is another object of the current invention to provide a novel vinyl meadowfoam monomer used as an intermediate in the preparation of the compounds of the present invention.

It is still another objective of the current invention to provide personal care compositions which contain an effective conditioning amount of the compounds of the current invention. That effective conditioning concentration will vary from 0.1 to 20% of the composition. The compounds of the present invention have outstanding compatibility with anionic, nonionic and cationic surfactant systems.

SUMMARY OF THE INVENTION

The present invention is directed to free radical polymers which contain a meadowfoam ester group as one of the functional groups polymerized. The compounds of the invention are prepared by the free radical polymerization of a novel meadowfoam monomer having a reactive vinyl group.

The unique structure of the meadowfoam results in these polymers with oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Meadowfoam has a unique distribution of acyl groups. That distribution is;

60–65% by weight $$-(CH_2)_3-CH=CH-(CH_2)_{13}-CH_3$$

12–20% by weight a mixture of $$-(CH_2)_3-CH=CH-(CH_2)_{15}-CH_3$$

and $$-(CH_2)_{11}-CH=CH-(CH_2)_7-CH_3$$

and

15–28% by weight $$-(CH_2)_3-CH=CH-(CH_2)_6-CH=CH-(C_2)_6-CH_3;$$

$R^2$ and $R^3$ are methyl or ethyl.

The compounds of the current invention conform to the following generic structure;

$$H-(\underset{R}{\overset{R}{C}}-CH_2)_a-(\underset{R}{\overset{1}{CH}}-CH_2)_b-(\underset{R}{\overset{2}{CH}}-CH_2)_c-(\underset{R}{\overset{3}{CH}}-CH_2)_d-(\underset{R}{\overset{4}{CH}}-CH_2)_e-(\underset{R}{\overset{5}{CH}}-CH_2)_f-H$$

wherein;

R is selected from the group consisting of CH3 and H;
a is an integer from 1 to 100;
b, c, and d are integers ranging from 0 to 100;
$R^1$ is

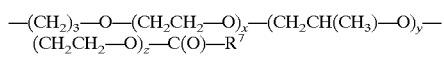

x, y and z are independently integers ranging from 0 to 20;
$R^7$ is derived from meadowfoam and is 60–65% by weight

12–20% by weight a mixture of

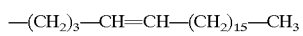

and

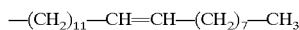

and

15–28% by weight

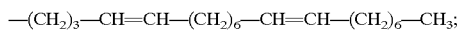

$R^2$ is —C(O)—O$^-$M$^+$
M is selected from H, Na, K, Li, and NH 4;
$R^3$ is

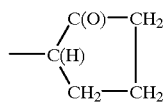

$R^4$ is

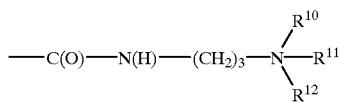

$R^{10}$, $R^{11}$ and $R^{12}$ are selected from H, methyl and ethyl;
$R^5$ is —C(O)—NH$_2$
$R^6$ is

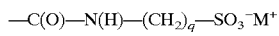

q is an integer ranging from 1 to 5.

The compounds of the current invention are prepared by the free radical reaction of a meadowfoam ester containing monomer and other monomers selected from the following;

$R^1$ is derived from a meadowfoam ester monomer conforming to the following structure;

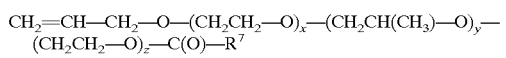

x, y and z are independently integers ranging from 0 to 20;
$R^7$ is derived from meadowfoam and is 60–65% by weight

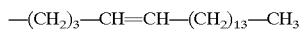

12–20% by weight a mixture of

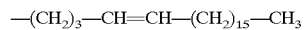

and

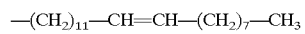

and

15–28% by weight

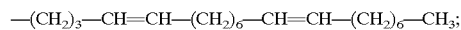

$R^2$ is derived from the following monomer CH$_2$=CH—C(O)—O$^-$M$^+$
Acrylic acid and methacrylic acid is available from Dow.
$R^3$ is derived from the following monomer;

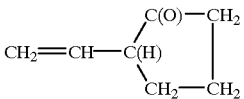

Vinyl pyrrolidone is available commercially from BASF.
$R^4$ is derived from the following monomer;

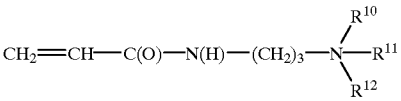

$R^{10}$, $R^{11}$ and $R^{12}$ are selected from H, methyl and ethyl;
These monomers are available from CPS Corporation.
$R^5$ is derived from the following monomer CH$_2$=CH—C(O)—NH$_2$
Acrylamide is available from Dow Chemical.
$R^6$ is derived from the following monomer;

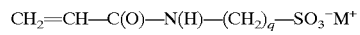

These materials are available from Lubrizol Inc.

These materials are reacted in a solvent, typically water under the influence of a free radical catalyst. Free radical polymerization is well known to those skilled in the art.

The meadowfoam derivative is prepared by the reaction of meadowfoam seed oil, or meadowfoam fatty acid with a allyl alcohol or allyl alcohol alkoxylate to obtain a vinyl meadowfoam ester which in a subsequent step is reacted either with itself or with the other monomers listed above.

A novel aspect of the present invention is the vinyl containing meadowfoam ester. Specifically, the meadowfoam ester of allyl alcohol alkoxylate is made by esterifying meadowfoam fatty acid with allyl alcohol or allyl alcohol alkoxylate in the presence of a suitable catalyst. The reaction is as follows:

$$CH_2=CH-CH_2-O-(CH_2CH_2-O)_{\overline{x}}-(CH_2CH(CH_3)-O)_{\overline{y}}-(CH_2CH_2-O)_{\overline{z}}-H \;+\; HO-C(O)-R^7$$

$$\downarrow$$

$$CH_2=CH-CH_2-O-(CH_2CH_2-O)_{\overline{x}}-(CH_2CH(CH_3)-O)_{\overline{y}}-(CH_2CH_2-O)_{\overline{z}}-C(O)-R^7 \;+\; H_2O$$

wherein:

x, y and z are independently integers ranging from 0 to 20;

$R^7$ is derived from meadowfoam and is 60–65% by weight $-(CH_2)_3-CH=CH-(CH_2)_{13}-CH_3$ 12–20% by weight a mixture of $-(CH_2)_3-CH=CH-(CH_2)_{15}-CH_3$ and $-(CH_2)_{11}-CH=CH-(CH_2)_7-CH_3$ and 15–28% by weight $-(CH_2)_3-CH=CH-(CH_2)_6-CH=CH-(CH_2)_6-CH_3;$

PREFERRED EMBOIDMENTS

In a preferred embodiment x, y, and z are all 0.

In a preferred embodiment x ranges from 4 to 20, y and z are 0.

In a preferred embodiment x ranges from 7 to 15, y and z are 0.

In a preferred embodiment x ranges from 4 to 20, y ranges from 4 to 20 and z ranges from 4 to 20.

In a preferred embodiment x is 0, y ranges from 4 to 20 and z is 0.

In a preferred embodiment x is 7, y is 0 and z is 0.

In a preferred embodiment x, y, and z are all 20.

In a preferred embodiment x, y, and z are all 7.

In a preferred embodiment b, c, d, e and f are all 0.

In a preferred embodiment b is 0.

In a preferred embodiment c is 0.

In a preferred embodiment d is 0.

In a preferred embodiment f is 0.

In a preferred embodiment d is 0.

In a preferred embodiment b and c are both 0.

In a preferred embodiment c and d are both 0.

In a preferred embodiment e and f are both 0.

In a preferred embodiment b and f are 0.

EXAMPLES

Raw Materials

Meadowfoam Oil

Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8.

The choice of triglyceride, acid or methyl ester does not change the structure of the resultant ester. It does however change the by-product produced. In the case of the triglyceride, glycerine is produced, in the case of the acid water is produced and in the case of the methyl ester methanol is produced.

Allyl Alcohol Alkoxylates

These compounds conform to the following structure:

$$CH_2=CH-CH_2-O-(CH_2CH_2-O)_x-(CH_2CH(CH_3)CH_2-O)_y-(CH_2CH_2-O)_z-H$$

| Example Number | x | y | z |
|---|---|---|---|
| 1 | 0 | 0 | 0 |
| 2 | 0 | 1 | 0 |
| 3 | 4 | 0 | 0 |
| 4 | 7 | 0 | 0 |
| 5 | 10 | 0 | 0 |
| 6 | 20 | 0 | 0 |
| 7 | 4 | 7 | 10 |
| 8 | 7 | 4 | 20 |
| 9 | 10 | 20 | 4 |
| 10 | 20 | 10 | 7 |
| 11 | 20 | 20 | 20 |
| 12 | 7 | 7 | 7 |

These materials are items of commerce available commercially from Siltech Corporation Toronto Ontario Canada, and Pelron Corporation Chicago, Ill.

Preparation of Vinyl Meadowfoam Esters

General Procedure

Meadowform esters are prepared by the reaction of the allyl alcohol alkoxylates example 1–12 with one mole of meadowfoam acid. The reaction mass is heated to 140 to 180 C and the theoretical amount of water is stripped off.

To 342.0 grams of meadowfoam acid is added to a clean glass vessel equipped with agitation and a thermometer. Next, the specified amount of the specified intermediate Examples 1–12 is added. The reaction mass is heated to 140 to 180 C and the theoretical amount of water distills off. The acid value becomes vanishingly low. The vinyl meadowfoam ester is used without additional purification.

Examples 13–32

|  | Grams | Example Number |
|---|---|---|
| Example 13 | 58.0 | 1 |
| Example 14 | 102.0 | 2 |
| Example 15 | 234.0 | 3 |
| Example 16 | 366.0 | 4 |
| Example 17 | 498.0 | 5 |
| Example 18 | 938.0 | 6 |
| Example 19 | 1087.0 | 7 |
| Example 20 | 1718.0 | 8 |
| Example 21 | 1912.1 | 9 |
| Example 22 | 1836.2 | 10 |

| | Grams | Example Number |
|---|---|---|
| Example 23 | 2998.3 | 11 |
| Example 24 | 1087.0 | 12 |

Meadowfoam Oil Derived

Meadowfoam esters are also prepared by the reaction of the allyl alcohol alkoxylates example 1–12 with one mole of meadowfoam oil. Meadowfoam oil is a triglyceride. The reaction mass is heated to 140 to 180 C and the theoretical amount of water is stripped off.

To 350.0 grams of meadowfoam oil is added to a clean glass vessel equipped with agitation and a thermometer. Next, the specified amount of the specified intermediate Examples 1–12 is added. The reaction mass is heated to 140 to 180 C and the theoretical amount of water distills off. The acid value becomes vanishingly low. The vinyl meadowfoam ester is used without additional purification.

| Example | Grams | Example Number |
|---|---|---|
| Example 25 | 58.0 | 1 |
| Example 26 | 102.0 | 2 |
| Example 27 | 234.0 | 3 |
| Example 28 | 366.0 | 4 |
| Example 29 | 498.0 | 5 |
| Example 30 | 938.0 | 6 |
| Example 31 | 1087.0 | 7 |
| Example 32 | 1718.0 | 8 |

Class 2 Vinyl Amino Compounds

Examples 33–37

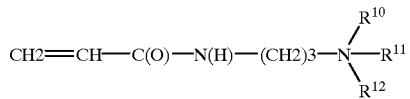

| Example | $R^{10}$ | $R^{11}$ | $R^{12}$ |
|---|---|---|---|
| 33 | Methyl | Methyl | Hydrogen |
| 34 | Methyl | Methyl | Methyl |
| 35 | Ethyl | Methyl | Hydrogen |
| 36 | Ethyl | Methyl | Methyl |
| 37 | Ethyl | Ethyl | Methyl |

Class 3 Vinyl Anionic Materials

Examples 38–41

| Example | q | M |
|---|---|---|
| 38 | 3 | H |
| 39 | 4 | H |
| 40 | 3 | Na |
| 41 | 3 | K |

Class 4 Vinyl Carboxylic Compounds

Example 42

Acrylic Acid CH2=CH—C(O)—OH

Class 5 Vinyl Lactones

Example 43

Vinyl pyrrolidone

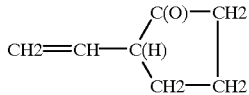

Class 6 Vinyl Amides

Example 44

Acrylamide CH2=CH—C(O)—NH2

Preparation of Meadowfoam Polymers

Examples 45–73
General Polymerization Procedure

The polymerization of the vinyl containing meadowfoam esters is achieved by utilizing free radical catalyst in a low oxygen containing solvent, most commonly water. The water is deionized and sparged with nitrogen to remove dissolved oxygen contained therein immediately prior to use. Then, the specified amount of the treated de-ionized water is added to a suitable glass vessel. Most commonly, 50 to 80% of the total weight of the batch is water. The specified amount of the specified monomers are then added under agitation. Nitrogen is continuously sparged and the temperature is raised to about 50 C. Once the temperature has reached 50 and the nitrogen has been bubbled through the reaction mass for thirty minutes, a free radical initiator is added. Many peracids, like t-butyl-perbenzoate, t-butyl-hydroperoxide and inorganic free radical initiators like stannic chloride can be used. The preferred initiator is azobisisobutylnitrile. The reaction is exothermic and cooling is used to keep the temperature below 90 C.

The molecular weight is monitored by viscosity and both increase as the reaction continues.

Example 45

To the specified number of grams (5,000 Gm.) of deionized water, which has just been spargred with nitrogen for 30 minutes, is added the specified amount (4,200 grams) of Class 1 monomer (Ex #17). Next add the specified amount (0 grams) of Class 2 monomer (Ex #25) followed by the specified amount (0 grams) of Class 3 monomer (Ex #29) followed by the specified amount (0 grams) of Class 4 monomer (Ex #33) followed by the specified amount (0 grams) of Class 5 monomer (Ex #34) followed by the specified amount (0 grams) of Class 6 monomer (Ex #35), under good agitation and nitrogen sparge. The temperature is raised to about 50 C. Once the temperature has reached 50 and the nitrogen has been bubbled through the reaction mass for thirty minutes, the specified amount of the specified catalyst (azobisisobutylnitrile) is added. The catalyst may be optimally added in smaller increments of one quarter of the total needed waiting 30 minutes between additions. The viscosity will raise as the polymerization occurs. The temperature raises to about 90 C and is cooled with cooling water as needed to prevent the temperature from reaching 90 C. The desired polymer is used as prepared.

Examples 46–73

The above procedure is repeated only substituting the specified amount and type of monomer, catalyst and water specified.

|         | Example 46 | Example 47 | Example 48 | Example 49 |
|---------|------------|------------|------------|------------|
| Class 1 | Ex # 17    | Ex # 18    | Ex # 19    | Ex # 20    |
|         | 4,200 Gm.  | 3,860 Gm.  | 12,747 Gm. | 1,714 Gm.  |
| Class 2 | Ex # 33    | Ex # 34    | Ex # 35    | Ex # 36    |
|         | 157.0 Gm.  | 171.0 Gm.  | 185.0 Gm.  | 216.0 Gm.  |
| Class 3 | Ex # 38    | Ex # 39    | Ex # 40    | Ex # 41    |
|         | 193.0 Gm.  | 207.0 Gm.  | 215.0 Gm.  | 231.0 Gm.  |
| Class 4 | Ex # 42    | Ex # 42    | Ex # 42    | Ex # 42    |
|         | 72.0 Gm.   | 0 Gm.      | 0 Gm.      | 0 Gm.      |
| Class 5 | Ex # 43    | Ex # 43    | Ex # 43    | Ex # 43    |
|         | 110.0 Gm.  | 1,100 Gm.  | 110.0 Gm.  | 0 Gm.      |
| Class 6 | Ex # 44    | Ex # 44    | Ex # 44    | Ex # 44    |
|         | 158.0 Gm.  | 1,580 Gm.  | 0 Gm.      | 0 Gm.      |
| Water   | 5,000 Gm.  | 10,000 Gm. | 20,000 Gm. | 5,000 Gms  |

Catalyst These examples used 0.05% by weight of batch of azobisisobutylnitrile

|         | Example 50 | Example 51 | Example 52 | Example 53 |
|---------|------------|------------|------------|------------|
| Class 1 | Ex # 21    | Ex # 22    | Ex # 23    | Ex # 24    |
|         | 13.5 Gm.   | 15.4 Gm.   | 67.8 Gm.   | 50.4 Gm.   |
| Class 2 | Ex # 33    | Ex # 34    | Ex # 35    | Ex # 37    |
|         | 157.0 Gm.  | 171.0 Gm.  | 185.0 Gm.  | 216.0 Gm.  |
| Class 3 | Ex # 38    | Ex # 38    | Ex # 38    | Ex # 38    |
|         | 0 Gm.      | 0 Gm.      | 0 Gm.      | 0 Gm.      |
| Class 4 | Ex # 42    | Ex # 42    | Ex # 42    | Ex # 42    |
|         | 0 Gm.      | 0 Gm.      | 0 Gm.      | 0 Gm.      |
| Class 5 | Ex # 43    | Ex # 43    | Ex # 43    | Ex # 43    |
|         | 0 Gm.      | 110.0 Gm.  | 1,100 Gm.  | 11.0 Gm.   |
| Class 6 | Ex # 44    | Ex # 44    | Ex # 44    | Ex # 44    |
|         | 0 Gm.      | 0 Gm.      | 0 Gm.      | 0 Gm.      |
| Water   | 250 Gm.    | 600 Gm.    | 3,000 Gm.  | 150 Gm.    |

Catalyst These examples used 0.05% by weight of batch of azobisisobutylnitrile

|         | Example 54 | Example 55 | Example 56 | Example 57 |
|---------|------------|------------|------------|------------|
| Class 1 | Ex # 25    | Ex # 26    | Ex # 27    | Ex # 28    |
|         | 4,200 Gm.  | 3,860 Gm.  | 12,747 Gm. | 1,714 Gm.  |
| Class 2 | Ex # 33    | Ex # 35    | Ex # 36    | Ex # 37    |
|         | 0 Gm.      | 157.0 Gm.  | 171.0 Gm.  | 185.0 Gm.  |
| Class 3 | Ex # 38    | Ex # 38    | Ex # 38    | Ex # 39    |
|         | 0 Gm.      | 0 Gm.      | 193.0 Gm.  | 207.0 Gm.  |
| Class 4 | Ex # 42    | Ex # 42    | Ex # 42    | Ex # 42    |
|         | 0 Gm.      | 0 Gm.      | 0 Gm.      | 72.0 Gm.   |
| Class 5 | Ex # 43    | Ex # 43    | Ex # 43    | Ex # 43    |
| Class 6 | Ex # 44    | Ex # 44    | Ex # 44    | Ex # 44    |
|         | 0 Gm.      | 0 Gm.      | 0 Gm.      | 0 Gm.      |
| Water   | 4,200 Gm.  | 5,000 Gm.  | 15,000 Gm. | 2,500 Gm.  |

Catalyst These examples used 0.05% by weight of batch of azobisisobutylnitrile

|         | Example 58 | Example 59 | Example 60 | Example 61 |
|---------|------------|------------|------------|------------|
| Class 1 | Ex # 29    | Ex # 30    | Ex # 31    | Ex # 32    |
|         | 1,355 Gm.  | 15,415 Gm. | 6,789 Gm.  | 5,043 Gm.  |
| Class 2 | Ex # 33    | Ex # 34    | Ex # 35    | Ex # 36    |
|         | 216.0 Gm.  | 1,570 Gm.  | 1,710 Gm.  | 1,850 Gm.  |
| Class 3 | Ex # 38    | Ex # 39    | Ex # 40    | Ex # 41    |
|         | 215.0 Gm.  | 231.0 Gm.  | 193.0 Gm.  | 207.0 Gm.  |
| Class 4 | Ex # 42    | Ex # 42    | Ex # 42    | Ex # 42    |
|         | 0 Gm.      | 0 Gm.      | 0 Gm.      | 0 Gm.      |
| Class 5 | Ex # 43    | Ex # 43    | Ex # 43    | Ex # 43    |
|         | 110.0 Gm.  | 110.0 Gm.  | 110.0 Gm.  | 1,100 Gm.  |
| Class 6 | Ex # 44    | Ex # 44    | Ex # 44    | Ex # 44    |
|         | 0 Gm.      | 0 Gm.      | 0 Gm.      | 158.0 Gm.  |
| Water   | 2,000 Gm.  | 22,000 Gm. | 10,000 Gm. | 10,000 Gm. |

Catalyst These examples used 0.05% by weight of batch of t-butyl-hydroperoxide (Lucidol TBHP-70-X)

|         | Example 62 | Example 63 | Example 64 | Example 65 |
|---------|------------|------------|------------|------------|
| Class 1 | Ex # 17    | Ex # 18    | Ex # 19    | Ex # 20    |
|         | 4,200 Gm.  | 3,860 Gm.  | 12,747 Gm. | 1,714 Gm.  |
| Class 2 | Ex # 35    | Ex # 34    | Ex # 33    | Ex # 37    |
|         | 0 Gm.      | 0 Gm.      | 0 Gm.      | 0 Gm.      |
| Class 3 | Ex # 38    | Ex # 38    | Ex # 38    | Ex # 38    |
|         | 0 Gm.      | 0 Gm.      | 0 Gm.      | 0 Gm.      |
| Class 4 | Ex # 42    | Ex # 42    | Ex # 42    | Ex # 42    |
|         | 0 Gm.      | 0 Gm.      | 0 Gm.      | 0 Gm.      |
| Class 5 | Ex # 43    | Ex # 43    | Ex # 43    | Ex # 43    |
|         | 4,200 Gm.  | 110.0 Gm.  | 30,000 Gm. | 100.0 Gm.  |
| Class 6 | Ex # 44    | Ex # 44    | Ex # 44    | Ex # 44    |
|         | 0 Gm.      | 0 Gm.      | 0 Gm.      | 0 Gm.      |
| Water   | 10,000 Gm. | 5,000 Gm.  | 55,000 Gm. | 1,000 Gm.  |

Catalyst These examples used 0.07% by weight of batch of t-butyl-hydroperoxide (Lucidol TBHP-70-X)

|         | Example 66 | Example 67 | Example 68 | Example 69 |
|---------|------------|------------|------------|------------|
| Class 1 | Ex # 21    | Ex # 22    | Ex # 23    | Ex # 24    |
|         | 135.5 Gm.  | 154.1 Gm.  | 67.9 Gm.   | 50.4 Gm.   |
| Class 2 | Ex # 33    | Ex # 33    | Ex # 33    | Ex # 33    |
|         | 1,570 Gm.  | 0 Gm.      | 0 Gm.      | 0 Gm.      |
| Class 3 | Ex # 38    | Ex # 39    | Ex # 40    | Ex # 41    |
|         | 0 Gm.      | 1,930 Gm.  | 0 Gm.      | 0 Gm.      |
| Class 4 | Ex # 42    | Ex # 42    | Ex # 42    | Ex # 42    |
|         | 0 Gm.      | 0 Gm.      | 720 Gm.    | 0 Gm       |
| Class 5 | Ex # 43    | Ex # 43    | Ex # 43    | Ex # 43    |
|         | 0 Gm.      | 0 Gm.      | 0 Gm.      | 1,100 Gm.  |
| Class 6 | Ex # 44    | Ex # 44    | Ex # 44    | Ex # 44    |
|         | 0 Gm.      | 0 Gm.      | 0 Gm.      | 0 Gm.      |
| Water   | 1,000 Gm.  | 1,000 Gm.  | 1,000 Gm.  | 2,000 Gm.  |

Catalyst These examples used 0.07% by weight of batch of t-butyl perbenzoate

|  | Example 70 | Example 71 | Example 72 | Example 73 |
|---|---|---|---|---|
| Class 1 | Ex # 32 | Ex # 31 | Ex # 30 | Ex # 29 |
|  | 420.0 Gm. | 386.0 Gm. | 1,274 Gm. | 171.4 Gm. |
| Class 2 | Ex # 36 | Ex # 35 | Ex # 36 | Ex # 37 |
|  | 216.0 Gm. | 2,160 Gm. | 2.16 Gm. | 2,160 Gm. |
| Class 3 | Ex # 38 | Ex # 39 | Ex # 40 | Ex # 41 |
|  | 0 Gm. | 0 Gm. | 0 Gm. | 0 Gm. |
| Class 4 | Ex # 42 | Ex # 42 | Ex # 42 | Ex # 42 |
|  | 0 Gm. | 0 Gm. | 0 Gm. | 0 Gm. |
| Class 5 | Ex # 43 | Ex # 43 | Ex # 43 | Ex # 43 |
|  | 110.0 Gm. | 1,100 Gm. | 11.0 Gm. | 0 Gm. |
| Class 6 | Ex # 44 | Ex # 44 | Ex # 44 | Ex # 44 |
|  | 0 Gm. | 0 Gm. | 0 Gm. | 0 Gm. |
| Water | 500 Gm. | 1,000 Gm. | 5,000 Gm. | 10,000 Gm. |

Catalyst These examples used 0.05% by weight of batch of t-butyl perbenzoate

Applications Data

Applications of the Compounds of The Invention

Compounds of this invention were compared to standard compounds commercially available using AATCC Test Method 117-1979. The color fastness heat test uses a 400 F (205 F) hot iron which is applied for 60 and 180 seconds. The color is rated on a 1–5 basis for yellowness, (5 being the most yellow).

| Compound | CAS Number | Yellowness |
|---|---|---|
| Class # 1 Compound | 68122-86-1 | 4 |
| Class # 2 Compound | 61789-81-9 | 4 |
| Class # 3 Compound | 65098-88-6 | 5 |
| Class # 4 Compound | 68308-45-2 | 4 |
| Example # 53 |  | 1 |
| Example # 48 |  | 2 |
| Example # 62 |  | 2 |

Wet Comb Out Test

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12–14 seconds.

| Rinse Conditioner (Wet Comb Out Test) | |
|---|---|
| Product | Time in Seconds |
| Product Example # 53 | 11 |
| Product Example # 48 | 13 |
| Stearyldimethylbenzyl ammonium chloride | 12 |

The compounds of the present invention are useful as softening, anti-tangle, and conditioning agents. They are nonirritating, substantive materials which are oxygen permeable. Their use is therefore recommended for use in personal care, textile and related applications.

The properties of these novel compounds containing silicone which makes them well suited for these applications is the fact that they are substantive to fibers, hair and skin and also very mild to the skin and eyes.

The compounds of the present invention are useful as softening, anti-tangle, and conditioning agents. They are nonirritating, substantive materials which are oxygen permeable. Their use is therefore recommended for use in personal care, textile and related applications.

The properties of these novel compounds containing silicone which makes them well suited for these applications is the fact that they are substantive to fibers, hair and skin and also very mild to the skin and eyes.

Another critical property of the compounds of the present invention is their outstanding oxidative stability. The compounds of the present invention, do not develop mal odor even when kept at elevated temperatures (50° C.) for extended periods (1 month).

What is claimed is:

1. A vinyl containing meadowfoam ester conforming to the following structure:

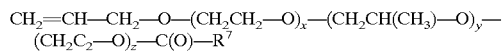

wherein x, y and z are independently integers ranging from 0 to 20;

$R^7$ is derived from meadowfoam and is

60–65% by weight

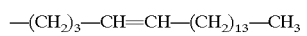

12–20% by weight a mixture of

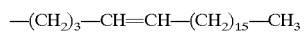

and

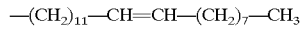

and

15–28% by weight

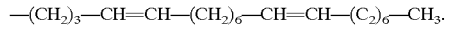

2. A vinyl containing meadowfoam ester of claim 1 wherein x, y, and z are all 0.

3. A vinyl containing meadowfoam ester of claim 1 wherein x ranges from 4 to 20, y is 0 and z is 0.

4. A vinyl containing meadowfoam ester of claim 1 wherein x ranges from 7 to 15 y is 0 and z is 0.

5. A vinyl containing meadowfoam ester of claim 1 wherein x ranges from 4 to 20, y ranges from 4 to 20 and z ranges from 4 to 20.

6. A vinyl containing meadowfoam ester of claim 1 wherein x is 0, y ranges from 4 to 20 and z is 0.

7. A vinyl containing meadowfoam ester of claim 1 wherein x is 7, y is 0 and z is 0.

8. A vinyl containing meadowfoam ester of claim 1 wherein x, y, and z are all 20.

9. A vinyl containing meadowfoam ester of claim 1 wherein x, y, and z are all 7.

10. A meadowfoam polymer conforming to the following structure;

$$H-(C(R)(R)-CH2)_a-(CH(R)-CH2)_b-(CH(R)-CH2)_c-(CH(R)-CH2)_d-(CH(R)-CH2)_e-(CH(R)-CH2)_f-H$$

with substituents $R^1, R^2, R^3, R^4, R^5, R^6$ at positions 1–6 respectively;

wherein;
R is selected from the group consisting of CH3 and H;
a is an integer from 1 to 100;
b, c, and d are integers ranging from 0 to 100;
$R^1$ is $$-(CH_2)_3-O-(CH_2CH_2-O)_x-(CH_2CH(CH_3)-O)_y-(CH_2CH_2-O)_z-C(O)-R^7$$

x, y and z are independently integers ranging from 0 to 20;
$R^7$ is derived from meadowfoam and is 60–65% by weight $$-(CH_2)_3-CH=CH-(CH_2)_{13}-CH_3$$

12–20% by weight a mixture of $$-(CH_2)_3-CH=CH-(CH_2)_{15}-CH_3$$

and $$-(CH_2)_{11}-CH=CH-(CH_2)_7-CH_3$$

and
15–28% by weight $$-(CH_2)_3-CH=CH-(CH_2)_6-CH=CH-(CH_2)_6-CH_3;$$

$R^2$ is $-C(O)-O^-M^+$
M is selected from H, Na, K, Li, and NH 4;
$R^3$ is $$-C(H)(C(O)-CH_2)(CH_2-CH_2)$$ (cyclic)

$R^4$ is $$-C(O)-N(H)-(CH_2)_3-N(R^{10})(R^{11})(R^{12})$$

$R^{10}$, $R^{11}$ and $R^{12}$ are selected from H, methyl and ethyl;
$R^5$ is $-C(O)-NH_2$
$R^6$ is $$-C(O)-N(H)-(CH_2)_q-SO_3^-M^+$$

q is an integer ranging from 1 to 5.

11. A meadowfoam polymer of claim 10 wherein b, c, d, e and f are all 0.

12. A meadowfoam polymer of claim 10 wherein b is 0.

13. A meadowfoam polymer of claim 10 wherein c is 0.

14. A meadowfoam polymer of claim 10 wherein d is 0.

15. A meadowfoam polymer of claim 10 wherein f is 0.

16. A meadowfoam polymer of claim 10 wherein d is 0.

17. A meadowfoam polymer of claim 10 wherein b and c are both 0.

18. A meadowfoam polymer of claim 10 wherein c and d are both 0.

19. A meadowfoam polymer of claim 10 wherein e and f are both 0.

20. A meadowfoam polymer of claim 10 wherein b and f are 0.

* * * * *